(12) United States Patent
Bartels et al.

(10) Patent No.: US 11,306,093 B2
(45) Date of Patent: Apr. 19, 2022

(54) PROCESS FOR PREPARATION OF 2-(6-NITROPYRIDIN-3-YL)-9H-DIPYRIDO[2,3-B;3',4'-D]PYRROLE

(71) Applicant: Hoffmann-La Roche Inc., Little Falls, NJ (US)

(72) Inventors: Bjoern Bartels, Basel (CH); Philipp Cueni, Basel (CH); Matthias Koerner, Basel (CH); Dieter Muri, Basel (CH)

(73) Assignee: Hoffmann-La Roche, Inc., Little Falls, NJ (US)

( * ) Notice: Subject to any disclaimer, the term of this patent is extended or adjusted under 35 U.S.C. 154(b) by 0 days.

(21) Appl. No.: 16/294,627

(22) Filed: Mar. 6, 2019

(65) Prior Publication Data

US 2019/0300529 A1    Oct. 3, 2019

Related U.S. Application Data

(63) Continuation of application No. PCT/EP2017/072062, filed on Sep. 4, 2017.

(30) Foreign Application Priority Data

Sep. 9, 2016   (EP) .................................... 16187960

(51) Int. Cl.
  *C07D 471/14*   (2006.01)
  *C07D 471/04*   (2006.01)

(52) U.S. Cl.
  CPC ......... *C07D 471/14* (2013.01); *C07D 471/04* (2013.01)

(58) Field of Classification Search
  CPC .................................................. C07D 471/14
  USPC .......................................................... 546/82
  See application file for complete search history.

(56) References Cited

U.S. PATENT DOCUMENTS

| 10,004,817 B2 | 6/2018 | Gobbi et al. | |
| 11,058,781 B2 | 7/2021 | Gobbi et al. | |
| 2004/0224997 A1 | 11/2004 | Smith et al. | |
| 2010/0056491 A1* | 3/2010 | Schumacher | C07D 471/04 514/210.21 |
| 2010/0239496 A1 | 9/2010 | Gangadharmath et al. | |
| 2011/0046378 A1 | 2/2011 | Kolb et al. | |
| 2011/0182812 A1 | 7/2011 | Szardenings et al. | |

(Continued)

FOREIGN PATENT DOCUMENTS

| WO | 2006/040451 | 4/2006 |
| WO | 2009/102498 A1 | 8/2009 |
| WO | 2009/151589 A1 | 12/2009 |

(Continued)

OTHER PUBLICATIONS

Alonso, Tetrahedron, 2008, 64, 3047-3301.*

(Continued)

*Primary Examiner* — Nizal S Chandrakumar
(74) *Attorney, Agent, or Firm* — Genentech, Inc.; Richard G. A. Bone

(57) ABSTRACT

A process for preparing the compound of formula I

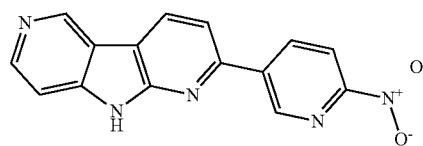

comprising:
a) coupling a compound of formula 2

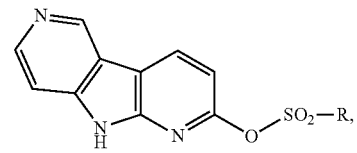

wherein a leaving group O—SO$_2$—R is selected from the triflate group, the tosylate group, the mesylate group, the besylate group, the nosylate group or the brosylate group, with a suitable boronic acid, a trifluoroborate or a boronic acid ester
under argon condition and in the presence of a catalyst and a base in a suitable solvent and then isolating the product as an acid addition salt
to afford the compound of formula Ia

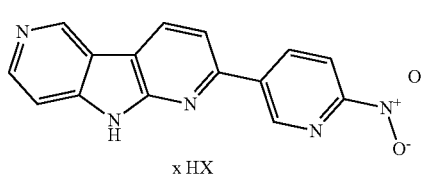

and
b) converting the acid addition salt of formula Ia
wherein the acid HX comprises suitable organic or inorganic acids into the compound of formula I (Continued)

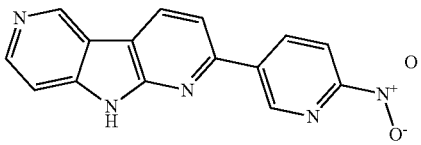

I by treatment with at least a stoichiometric equivalent of a suitable base.

15 Claims, No Drawings

(56) References Cited

U.S. PATENT DOCUMENTS

| | | |
|---|---|---|
| 2012/0302755 A1 | 11/2012 | Szardenings et al. |
| 2015/0368244 A1 | 12/2015 | Dyke et al. |

FOREIGN PATENT DOCUMENTS

| | | |
|---|---|---|
| WO | 2010/011964 A2 | 1/2010 |
| WO | 2010/111303 A2 | 9/2010 |
| WO | 2011/073263 A1 | 6/2011 |
| WO | 2013/006634 A2 | 1/2013 |
| WO | 2015/052105 A1 | 4/2015 |
| WO | 2017/042114 A1 | 3/2017 |

OTHER PUBLICATIONS

Quan, Eur. J. Org. Chem. 2013, 7175-7183.*
Kassanova Russian Chemical Bulletin, International Edition, vol. 65, No. 11, pp. 2559-2567, Nov. 2016.*
Beletskaya, Coordination Chemistry Reviews 385 (201 9) 137-173.*
Bartels, B. et al., Development of a safe and scalable route towards a tau PET tracer precursor, Bioorg. Med. Chem. 26:970-976 (Jan. 1, 2018).
Gobbi, L., et al., "Identification of Three Novel Radiotracers for Imaging Aggregated Tau in Alzheimer's Disease with Positron Emission Tomography" J Med Chem 60:7350-7370 (Jun. 27, 2017).
Honer, M., et al., "Preclinical Evaluation of 18F-RO6958948, 11C-RO6931643, and 11C-RO6924963 as Novel PET Radiotracers for Imaging Tau Aggregates in Alzheimer Disease" J Nucl Med 59:675-681 (Jun. 6, 2017).
"International Preliminary Report on Patentability—PCT/EP2017/072062":pp. 1-7 (dated Mar. 21, 2019).
"International Search Report—PCT/EP2017/072062":pp. 1-13 (dated Nov. 7, 2017).
Beletskaya, I., et al., "Review: the Suzuki-Miyaura reaction after the Nobel prize" Coord Chem Reviews 385:137-173 (Apr. 15, 2019).
Kassanova, A., et al., "Pyridinyl trifluoromethanesulfonates: preparation methods and use in organic synthesis" Russian Chem Bulletin 65(11):2559-2567 (Nov. 1, 2016).

* cited by examiner

PROCESS FOR PREPARATION OF 2-(6-NITROPYRIDIN-3-YL)-9H-DIPYRIDO [2,3-B;3',4'-D]PYRROLE

CROSS-REFERENCE TO RELATED APPLICATIONS

This application is a continuation of, and claims priority to, International Patent Application No. PCT/EP2017/072062, filed on Sep. 4, 2017, which claims benefit of priority to European Patent Application No. 16187960.6, filed on Sep. 9, 2016. The entire contents of each of the above patent applications are hereby incorporated by reference.

SUMMARY

The present invention relates to a process for preparation of 2-(6-nitropyridin-3-yl)-9H-dipyrido[2,3-b;3',4'-d]pyrrole

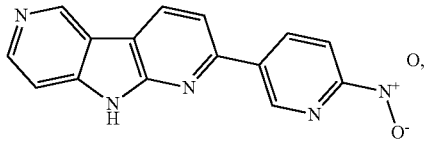

which is a precursor for the preparation of [$^{18}$F]-2-(6-fluoro-pyridin-3-yl)-9H-dipyrido[2,3-b;3',4'-d]pyrrole.

[$^{18}$F]-2-(6-Fluoro-pyridin-3-yl)-9H-dipyrido[2,3-b;3',4'-d]pyrrole, its processes for preparation and its use in binding and imaging of tau aggregates and related beta-sheet aggregates including besides other beta-amyloid aggregates or alpha-synuclein aggregates, especially for its use in binding and imaging of tau aggregates in Alzheimer's patients are described in WO2015/052105.

In WO2015/052105 2-(6-nitropyridin-3-yl)-9H-dipyrido [2,3-b;3',4'-d]pyrrole was used as precursor of the corresponding PET tracer. It was prepared from 2-chloro-dipyrido[2,3-b;3',4'-d]pyrrole-9-carboxylic acid tert-butyl ester

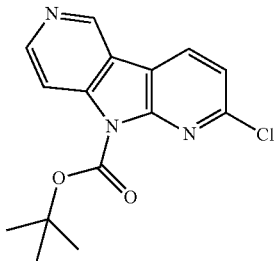 [SMILES: CC(C)(C)OC(=O)n1c2ccncc2c2ccc(Cl)nc21]

with 2-nitropyridine-5-boronic acid pinacol ester

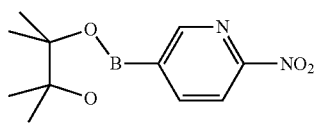

with a combination of 1,1'-bis(diphenylphosphino)ferrocene-palladium(II)dichloride dichloromethane complex and K$_2$CO$_3$ in DMF.

This process, described in WO2015/052105, is a very short access route starting from expensive starting materials and resulting in variable yields though. Furthermore, a Boc-protecting group is necessary to facilitate final coupling, which nevertheless results in a mixture of several products. The desired, highly insoluble product has to be purified by tedious preparative chromatography and recrystallization which leads to significant loss of material.

Therefore, it was necessary to find a safe and reliable process starting from readily available starting materials which gives access to the compound of formula I in reproducible yield and high purity.

The new process can be described as follows:

The present compound of formula I

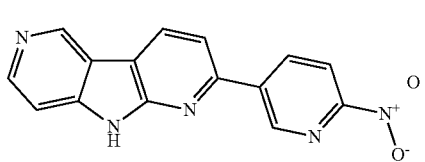

can be prepared by processes described below, which processes comprise a) coupling a compound of formula 2, wherein the sulfonyl group (SO$_2$—R) is selected from the triflyl group (TO, the tosyl group (Ts), the mesyl group (Ms), the besyl group, the nosyl group (Ns) or the brosyl group (Bs)

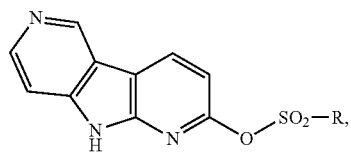

for example 9H-pyrrolo[2,3-b:4,5-c']dipyridin-2-yl trifluoromethanesulfonate, with a suitable boronic acid, a trifluoroborate or a boronic acid ester, such as 2-nitropyridine-5-boronic acid pinacol ester, under argon conditions and in the presence of catalytic amounts of a suitable transition metal complex, e.g. a palladium complex such as PdCl$_2$(xantphos) or Pd$_2$(dba)$_3$, a suitable base, such as potassium fluoride, and a polar solvent, such as THF, 2-Me-THF or dioxane, and isolating the product as acid addition salt by treatment with any suitable acids, such as acetic acid, trifluoroacetic acid, cinnamic acid, oxalic acid, tartaric acid, hydrochloric acid, hydrobromic acid, sulfuric acid or phosphoric acid, to afford the compound of formula Ia

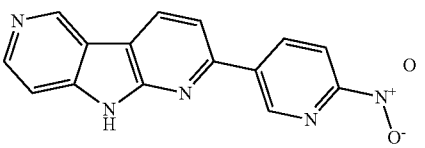

x HX and b) converting the obtained acid addition salt of formula Ia

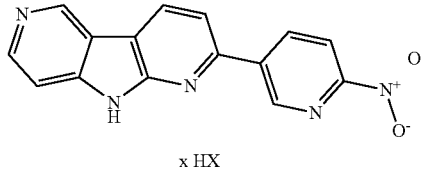

x HX wherein the acid HX comprises any suitable organic or inorganic acids, such as acetic acid, trifluoroacetic acid, cinnamic acid, oxalic acid, tartaric acid, hydrochloric acid, hydrobromic acid, sulfuric acid, phosphoric acid and the like, and x indicates that a stoichiometric equivalent of HX other than 1 may be present, into the compound of formula I

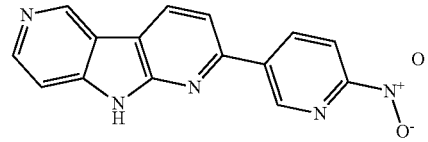

by treatment with at least a stoichiometric equivalent of a suitable base, such as sodium or potassium hydroxide, trimethylamine, potassium carbonate, sodium bicarbonate, ammonia, triethylamine and the like.

The end product [$^{18}$F]-2-(6-fluoro-pyridin-3-yl)-9H-dipyrido[2,3-b;3',4'-d]pyrrole

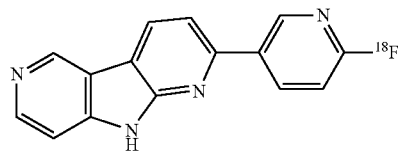 [SMILES: [18F]c1ccc(-c2ccc3c(n2)[nH]c2ccncc23)cn1]

may then be obtained as described in WO2015/052105 by dissolving a compound of formula I in dimethylsulfoxide and treating it with [$^{18}$F]fluoride/K[2,2,2]/K$_2$CO$_3$.

The following scheme 1 describes the processes for the preparation of a compound of formula I in more detail. The starting materials are known compounds or may be prepared according to methods known in the art.

The preparation of a compound of formula I of the present invention may be carried out in sequential or convergent synthetic routes. The skills required for carrying out the reactions and purifications of the resulting products are known to those skilled in the art. The substituents and indices used in the following description of the processes have the significance given herein before unless indicated to the contrary.

In more detail, the compound of formula I can be manufactured by the methods given below, by the methods given in the examples or by analogous methods. Appropriate reaction conditions for the individual reaction steps are known to a person skilled in the art. The reaction sequence is not limited to the one displayed in scheme 1, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

Abbreviations

Tf=Triflyl group, —SO$_2$CF$_3$
Ts=Tosyl group, —SO$_2$C$_6$H$_4$CH$_3$
Ms=Mesyl group, —SO$_2$CH$_3$
Besyl group=—SO$_2$C$_6$H$_5$
Ns=Nosyl group, —SO$_2$C$_6$H$_4$-o-NO$_2$
Bs=Brosyl group, —SO$_2$C$_6$H$_4$-p-Br
PdCl$_2$(xantphos)=Dichloro[9,9-dimethyl-4,5-bis(diphenylphosphino)xanthene]palladium(II)
Pd$_2$dba$_3$=Tris(dibenzylideneacetone)dipalladium(0)

Scheme 1

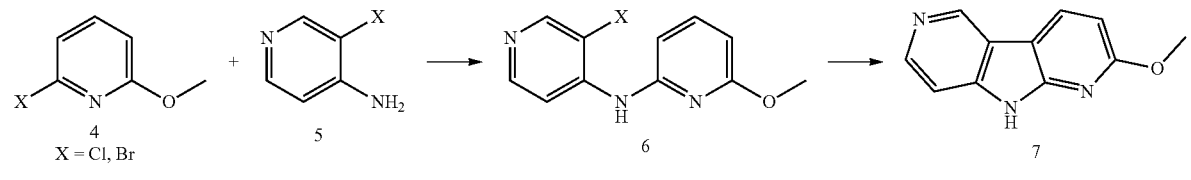

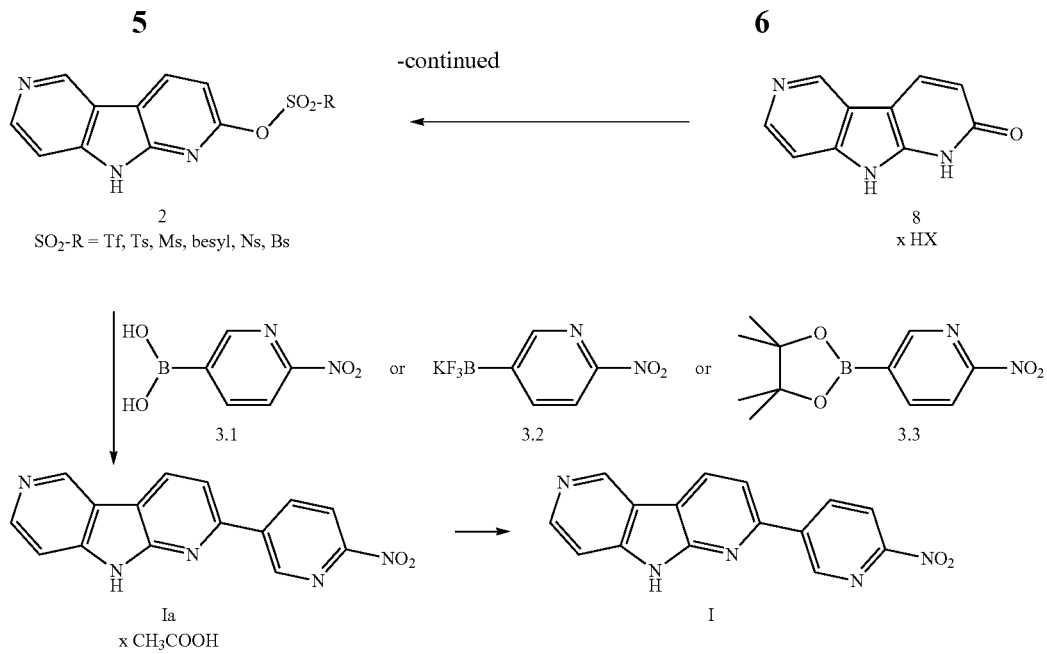

According to scheme 1, a compound of formula I can be prepared starting from 2-halo-6-methoxypyridines 4 (X=Cl, Br) and 3-halo-pyridin-4-amines 5 (X=Cl, Br). Transition-metal catalysed cross-coupling reaction using a catalyst system such as PdCh(xantphos) and a base such as cesium carbonate in a suitable solvent such as THF, 2-Me-THF or 1,4-dioxane at ambient or elevated temperature results in bipyridylamines 6 (X=Cl, Br). Intramolecular cyclisation can be performed using a catalyst system like e.g. such as Pd(OAc)$_2$ and tri-tert-butylphosphonium tetrafluoroborate and a base such as potassium carbonate in a suitable solvent such as DMF or DMA at ambient or elevated temperature to afford 1,6-diazacarbazole intermediate 7. Cleavage of the methoxy group can be achieved by treatment with a strong acid such as hydrobromic acid in a solvent such as acetic acid at ambient or elevated temperature resulting in 1,6-diazacarbazolin-2-one intermediate 8, isolated as, e.g., hydrobromic acid salt. Conversion of 1,6-diazacarbazolin-2-one intermediate 8 into an activated 2-hydroxy-1,6-diazacarbazole 2 (with SO$_2$—R being e.g., Tf, Ts, Ms, besyl, Ns, Bs) can be accomplished by treatment of intermediate 8 with an activating reagent such as N,N-bis(trifluoromethyl-sulfonyl)aniline (for SO$_2$—R=Tf) in presence of a base such as N,N-diisopropylethylamine in a suitable solvent such as DMF at temperatures between 0° C. and 50° C. Final transformation into the compound of formula I can be done by a direct transition metal-catalyzed cross-coupling reaction using a suitable boronic acid, a trifluoroborate or a boronic acid ester such as 2-nitropyridine-5-boronic acid pinacol ester, a catalyst system such as PdCl$_2$ (xantphos) and a base such as potassium fluoride in a suitable solvent such as THF, 2-Me-THF or 1,4-dioxane at ambient or elevated temperature. Treatment with an acid such as acetic acid enables isolation of the product as salt such as acetate Ia. Treatment with a base such as triethylamine in a solvent such as methanol or DMSO eventually liberates the compound of formula I as free base. Further bases may be used such as sodium or potassium hydroxide, trimethylamine, potassium carbonate, sodium bicarbonate, ammonia, and the like.

The above described 6-step synthesis route is based on readily available starting materials and reagents. It can be performed free of any chromatographic purification which is an important advantage for poorly soluble compounds as the intermediates and the final product described in scheme 1. The compound of formula I is obtained in >10% total isolated yield which corresponds to ~70% isolated yield for each reaction step. Further details can be found by reference to the preparations and examples herein below.

Isolation and Purification of the Compounds

Isolation and purification of the compounds and intermediates described herein can be performed, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be found by reference to the preparations and examples herein below. However, other equivalent separation or isolation procedures could, of course, also be used.

Salts of Compound of Formula I

The compound of formula I is basic and may be converted to a corresponding acid addition salt. The conversion is accomplished by treatment with at least a stoichiometric amount of an appropriate acid, such as hydrochloric acid, hydrobromic acid, sulfuric acid, phosphoric acid and the like, and organic acids such as acetic acid, propionic acid, pyruvic acid, oxalic acid, malic acid, malonic acid, succinic acid, maleic acid, fumaric acid, tartaric acid, citric acid, benzoic acid, cinnamic acid, methanesulfonic acid, p-toluenesulfonic acid, salicylic acid and the like. Typically, the free base is dissolved in an organic solvent such as diethyl ether, ethyl acetate, chloroform, ethanol or methanol and the like, and the acid added in a similar solvent. The temperature is maintained between 0° C. and 50° C. The resulting salt precipitates spontaneously or may be precipitated by addition of a less polar solvent.

The acid addition salts of the compound of formula I may be converted to the corresponding free base by treatment with at least a stoichiometric equivalent of a suitable base such as sodium or potassium hydroxide, potassium carbonate, sodium bicarbonate, ammonia, triethylamine and the like.

EXPERIMENTAL SECTION

Example 1

2-(6-Nitropyridin-3-yl)-9H-dipyrido[2,3-b;3',4'-d]pyrrole

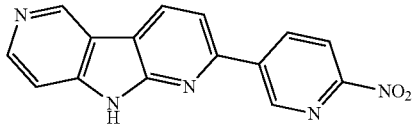 [SMILES: O=[N+]([O-])c1ccc(-c2ccc3c(n2)[nH]c2ccncc23)cn1]

Step 1:
N-(3-Chloropyridin-4-yl)-6-methoxypyridin-2-amine

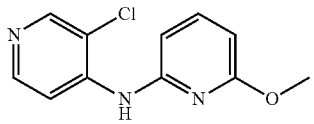 [SMILES: COc1cccc(Nc2ccncc2Cl)n1]

A 2 L four-necked sulfonation flask was purged with argon and charged with 1,4-dioxane (560 mL). 2-Chloro-6-methoxypyridine (25.0 g, 174 mmol), 3-chloropyridin-4-amine (27.5 g, 214 mmol) and cesium carbonate (78.8 g, 242 mmol) were consecutively added under argon. The suspension was stirred at ambient temperature for 30 min. Dichloro[9,9-dimethyl-4,5-bis(diphenylphosphino)xanthene]palladium(II) (6.9 g, 9.13 mmol) in 1,4-dioxane (65 mL) was added and the reaction mixture was heated to 100° C. for 65 h. A second portion of cesium carbonate (20 g, 61 mmol) and dichloro[9,9-dimethyl-4,5-bis(diphenylphosphino)-xanthene]palladium(II) (2.0 g, 2.65 mmol) in 1,4-dioxane (20 mL) were added and stirring at 100° C. was continued for another 3 h. Heating was discontinued and toluene (645 mL) was added. After cooling to ambient temperature, the reaction mixture was filtrated particle-free using a microfiber filter and the filter cake was washed with toluene (300 mL). The solvent of the clear yellowish filtrate was evaporated under reduced pressure and the residue was dried at 5 mbar. A solution of the obtained yellow solid in methanol (375 mL) was treated slowly with water (250 mL) over a period of 30 min. The mixture was stirred at ambient temperature for 30 min and at 0-5° C. (ice bath) for another 4 h. The formed crystalline material was filtered off, washed with a methanol/water mixture 1:2 (v/v) (180 mL) and subsequently dried at 65° C./5 mbar to obtain the desired product as light yellow solid (34.1 g, 80.6%). $^1$H NMR (400 MHz, DMSO-$d_6$) δ 3.85 (s, 3H), 6.40 (dd, J=0.7, 8.1 Hz, 1H), 6.90 (dd, J=0.7, 7.8 Hz, 1H), 7.64 (t, J=7.9 Hz, 1H), 8.29 (d, J=5.6 Hz, 1H), 8.36 (d, J=5.6 Hz, 1H), 8.45 (s, 1H), 8.76 (br s, 1H), LC-MS m/z 236.1 [M+H]$^+$, HPLC (260 nm) 97.0 area-%.

Step 2: 2-Methoxy-9H-pyrrolo[2,3-b:4,5-c']dipyridine

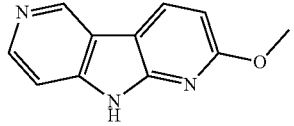

A 250 mL four-necked sulfonation flask was purged with argon and charged consecutively with palladium (II) acetate (500 mg, 2.23 mmol), tri-tert-butylphosphonium tetrafluoroborate (750 mg, 2.59 mmol) and DMA (20 mL). This mixture was stirred under argon at ambient temperature for 15 min. N-(3-chloropyridin-4-yl)-6-methoxypyridin-2-amine (10.0 g, 42.4 mmol), potassium carbonate (12 g, 86.8 mmol) and DMA (80 mL) were added and the reaction mixture was heated to 135° C. (bath temperature) and vigorously stirred for 18 h at this temperature. The dark reaction mixture was cooled to ambient temperature, diluted with ethyl acetate/ethanol 9:1 (v/v; 100 mL) and filtrated particle-free using a microfiber filter. The filter cake was washed with little ethyl acetate and the filtrate was evaporated under reduced pressure at 75° C. The yellow residue was dried at 75° C./5 mbar and re-dissolved in dioxane (250 mL) and ethyl acetate/methanol 8:2 (v/v; 250 mL) at elevated temperature (up to 75° C.). The yellow turbid solution was cooled to ambient temperature, charged to conditioned silica gel (50 g) and eluted with ethyl acetate/methanol 9:1 (v/v; 180 mL). The clear brownish filtrate was evaporated at 60° C. and the oily semi-crystalline residue was treated with tert-butyl methyl ether (50 mL). n-Heptane (35 mL) was added within 10 min and the suspension was stirred at ambient temperature for 1 h. The solid residue was filtered off, washed with n-heptane and dried at 60° C./5 mbar to obtain the desired product as white solid (5.1 g, 59.3%). $^1$H NMR (400 MHz, DMSO-$d_6$) δ 3.96 (s, 3H), 6.75 (d, J=8.6 Hz, 1H), 7.41 (dd, J=1.1, 5.6 Hz, 1H), 8.39 (d, J=5.6 Hz, 1H), 8.49 (d, J=8.3 Hz, 1H), 9.23 (d, J=0.8 Hz, 1H), 12.21 (br s, 1H), LC-MS m/z 200.2 [M+H]$^+$, GC 97.8 area-%.

Step 3: 1,9-Dihydro-dipyrido[2,3-b;3',4'-d]pyrrol-2-one hydrobromide

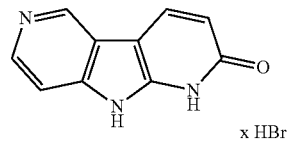 [SMILES: O=c1ccc2c([nH]1)[nH]c1ccncc12]

A 250 mL four-necked sulfonation flask was charged with 2-methoxy-9H-pyrrolo[2,3-b:4,5-c']dipyridine (5.0 g, 25.1 mmol). Acetic acid (40 mL) was added and the suspension was treated with hydrobromic acid (33 wt. % in AcOH, 20 mL, 114 mmol), heated to 80° C. and stirred for 18 h at this temperature. The white voluminous suspension was cooled to ambient temperature, treated with ethyl acetate (90 mL), stirred for 15 min and filtrated. The white residue was washed consecutively with little ethyl acetate and n-heptane and subsequently dried at 60° C./5 mbar to obtain the desired product as white solid (7.6 g, 87.3%) which was used in the next step without further purification. ¹H NMR (400 MHz, DMSO-d₆) δ 6.78 (d, J=8.6 Hz, 1H), 7.94 (dd, J=0.6, 6.7 Hz, 1H), 8.63 (d, J=6.4 Hz, 1H), 8.64 (d, J=8.6 Hz, 1H), 9.62 (s, 1H), 13.28 (br s, 1H), 14.80 (br s, 1H), LC-MS m/z 186.1 [M+H]⁺ of free base.

Step 4: 9H-Pyrrolo[2,3-b:4,5-c']dipyridin-2-yl trifluoromethanesulfonate

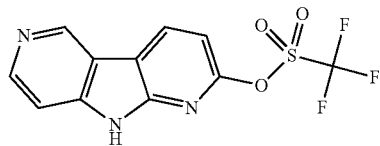 [SMILES: O=S(=O)(Oc1ccc2c(n1)[nH]c1ccncc12)C(F)(F)F]

A 500 mL four-necked sulfonation flask was purged with argon and charged with DMF (80 mL). 2-Oxo-2,9-dihydro-1H-pyrrolo[2,3-b:4,5-c']dipyridine-6,9-diium bromide (8.0 g, 23.1 mmol) and N,N-diisopropylethylamine (17.5 ml, 100 mmol) were added consecutively. The reaction mixture was cooled to 0-5° C. (ice bath) and treated with N,N-bis(trifluoromethyl-sulfonyl)aniline (12.5 g, 35 mmol) and DMF (10 mL). After warming up to ambient temperature stirring was continued for 45 min. At 5° C. a second portion of N,N-bis(trifluoromethyl-sulfonyl)aniline (4.2 g, 11.8 mmol) and DMF (10 mL) was added and stirring was continued at ambient temperature for 1 h. The orange suspension was treated with potassium bicarbonate (12 g, 129 mmol) and water (40 mL) and stirred at 50° C. for 18 h. Water (100 mL) was added within 15 min and the reaction mixture was cooled to 0-5° C. (ice bath) and stirred at this temperature for 1 h. The precipitate was filtered off and washed with water (50 mL) and n-heptane (50 mL) and was dried at 60° C./5 mbar to obtain the desired product as beige solid (7.4 g, 97.5%). ¹H NMR (400 MHz, DMSO-d₆) δ 7.46 (d, J=8.3 Hz, 1H), 7.55 (dd, J=0.9, 5.8 Hz, 1H), 8.57 (d, J=5.6 Hz, 1H), 8.95 (d, J=8.1 Hz, 1H), 9.47 (d, J=1.0 Hz, 1H), 12.83 (br s, 1H), LC-MS m/z 318.1 [M+H]⁺, HPLC (260 nm) 96.3 area-%.

Step 5: 2-(6-Nitropyridin-3-yl)-9H-pyrrolo[2,3-b:4,5-c']dipyridine acetate

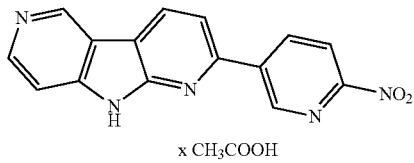 [SMILES: O=[N+]([O-])c1ccc(-c2ccc3c(n2)[nH]c2ccncc23)cn1]

x CH₃COOH

A 4.5 L four-necked sulfonation flask was purged with argon and charged consecutively with 9H-pyrrolo[2,3-b:4,5-c']dipyridin-2-yl trifluoromethane sulfonate (57.2 g, 180 mmol), 2-nitro-5-(4,4,5,5-tetramethyl-1,3,2-dioxaborolan-2-yl)pyridine (86.2 g, 345 mmol), potassium fluoride (114 g, 1.96 mol), 1,4-dioxane (1.40 L) and water (570 ml) and was stirred under argon at ambient temperature for 15 min. Then dichloro[9,9-dimethyl-4,5-bis(diphenylphosphino)xanthene]palladium(II) (22.8 g, 30.2 mmol) in 1,4-dioxane (280 mL) was added and the reaction mixture was stirred at 88-90° C. for 4.5 h. After cooling to ambient temperature, the reaction mixture was treated with ethanol (1.7 L) and stirred at 0-5° C. (ice bath) for 4 h. The precipitate was filtered off and washed with ethyl acetate (800 mL). The wet dark-brown solid was dissolved in refluxing acetic acid (800 mL), hot filtrated under vacuo and washed with hot acetic acid (40 mL). The clear dark solution was warmed up to 80° C., cooled to ambient temperature and stirred at this temperature for 20 h. The crystals were filtered off and washed consecutively with acetic acid/ethyl acetate 1:1 (200 mL), ethyl acetate (500 mL) and n-pentane (500 mL) and dried at 60° C./5 mbar to obtain 27 g of a yellow-brownish crude product (HPLC (260 nM): 99.6 area-%). The crude acetate (27 g) was suspended in acetic acid (540 mL) and water (27 mL) and heated to reflux. The hot and slightly turbid solution was hot (100° C.) filtrated particle-free under vacuo using a microfiber filter and the brown residue was washed with acetic acid (20 mL). The filtrate was warmed up again until a clear brown solution was present which was cooled to ambient temperature and stirred at that temperature for 18 h. The voluminous suspension was filtrated and the crystalline residue was washed consecutively with acetic acid/ethyl acetate 1:1 (150 mL), ethyl acetate (500 mL) and n-pentane (500 mL) and dried at 60° C./5 mbar to obtain 19.6 g of a dark yellow crude product (HPLC (260 nM) 99.5 area-%). The crude product was suspended in acetic acid (390 mL) and water (19.5 mL) and heated to reflux. The clear red solution was cooled to 80-90° C. and charged with charcoal (5 g). After heating to reflux, the suspension was filtrated particle-free under vacuo using a microfiber filter and the charcoal residue was washed with acetic acid (45 mL). The clear yellow filtrate was partly evaporated at 55° C. (ca. 100 mL) and to the resulting slurry was added ethyl acetate (230 mL). After cooling to ambient temperature the slurry was filtered off and the crystals were washed with ethyl acetate (300 mL) and n-pentane (250 mL). After drying at 60° C./5 mbar the desired product was obtained as yellow crystalline powder (17.2 g, 27.1%). ¹H NMR (400 MHz, DMSO-d₆) δ 1.91 (s, 3H), 7.53 (dd, J=1.1, 5.6 Hz, 1H), 8.21 (d, J=8.1 Hz, 1H), 8.48 (d, J=8.3 Hz, 1H), 8.54 (d, J=5.6 Hz, 1H), 8.85 (d, J=8.3 Hz, 1H), 8.95 (dd, J=2.2, 8.6 Hz, 1H), 9.44-9.46 (m, 2H), 11.97 (br s, 1H), 12.56 (br s, 1H), LC-MS m/z 292.2 [M+H]⁺ (free base), HPLC (260 nm) 99.8 area-%.

Step 6: 2-(6-Nitropyridin-3-yl)-9H-dipyrido[2,3-b;3',4'-d]pyrrole

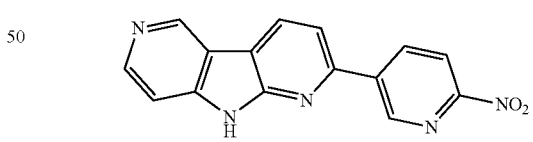

A 500 mL four-necked sulfonation flask was purged with argon and charged with 2-(6-nitropyridin-3-yl)-9H-pyrrolo[2,3-b:4,5-c']dipyridine acetate (15.50 g, 44.1 mmol). Methanol (310 ml) and triethylamine (9.5 ml, 68.2 mmol) were added. The reaction mixture was heated up to 60-65° C. and stirred for 1 h. After cooling to ambient temperature stirring was continued for another 2 h. The suspension was filtrated and the yellow solid was washed with little methanol and dried at 65° C./5 mbar. The crude product was treated with water (60 mL) and ultrasonicated until a homogeneous suspension was obtained. Water and residual methanol were evaporated at 22-25° C. (100-20 mbar) over a period of 16 h. The wet residue was dried at 60° C./5 mbar until constant weight and the product was obtained as yellow solid (12.5 g, 96.3%). $^1$H NMR (400 MHz, DMSO-d$_6$) δ 7.52 (dd, J=1.1, 5.6 Hz, 1H), 8.20 (d, J=8.3 Hz, 1H), 8.48 (d, J=8.6 Hz, 1H), 8.54 (d, J=5.6 Hz, 1H), 8.84 (d, J=8.1 Hz, 1H), 8.95 (dd, J=2.2, 8.6 Hz, 1H), 9.39-9.50 (m, 2H), 12.53 (s, 1H), LC-MS m/z 292.2 [M+H]$^+$, HPLC (260 nm) 99.2 area-%.

What is claimed:

1. A process for preparing a compound of formula I, wherein the process comprises:

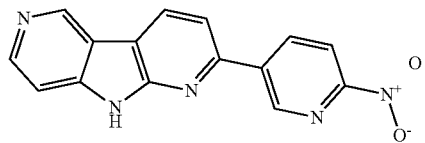

a) coupling a compound of formula 2

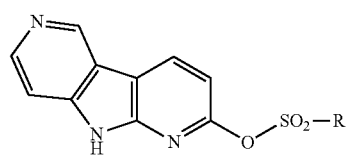

with a boron reagent selected from

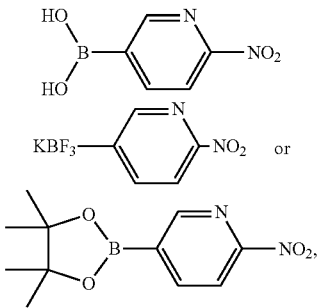

under argon condition in the presence of a catalytic amount of a transition metal complex and a first base in a polar solvent, wherein the group O—SO$_2$—R is selected from triflate, tosylate, mesylate, besylate, nosylate, and brosylate;

isolating the product of the coupling as an acid addition salt by treatment with an acid HX to afford a compound of formula Ia, wherein HX is an organic or inorganic acid,

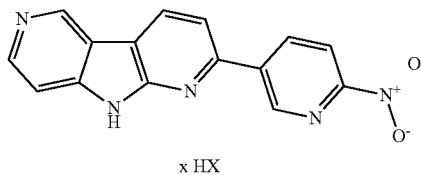

and b) converting the acid addition salt of formula Ia, into the compound of formula I by treatment with at least a stoichiometric equivalent of a second base.

2. The process of claim 1, wherein the compound of formula 2 is 9H-pyrrolo[2,3-b:4,5-c']dipyridin-2-yl trifluoromethanesulfonate.

3. The process of claim 1, wherein the boron reagent is 2-nitro-5-(4,4,5,5-tetramethyl-1,3,2-dioxaborolan-2-yl)pyridine.

4. The process of claim 1, wherein the transition metal complex is dichloro[9,9-dimethyl-4,5-bis(diphenylphosphino)xanthene]palladium(II).

5. The process of claim 1, wherein the first base is potassium fluoride.

6. The process of claim 1, wherein the polar solvent is selected from THF, 2-Me-THF and dioxane.

7. The process of claim 1, wherein the organic or inorganic acid is acetic acid, trifluoroacetic acid, cinnamic acid, oxalic acid, tartaric acid, hydrochloric acid, hydrobromic acid, sulfuric acid or phosphoric acid.

8. The process of claim 1, wherein the second base is sodium hydroxide, potassium hydroxide, trimethylamine, triethylamine, potassium carbonate, sodium bicarbonate or ammonia.

9. The process of claim 1 wherein the transition metal complex is tris(dibenzylideneacetone)dipalladium(0).

10. A process for synthesizing [$^{18}$F]-2-(6-fluoro-pyridin-3-yl)-9H-dipyrido [2,3-b;3',4'-d]pyrrole, the process comprising:

synthesizing a compound of formula I, according to the process of claim 1; and dissolving the compound of formula I in dimethylsulfoxide and treating it with [$^{18}$F]fluoride.

11. The process of claim 1, wherein the compound of formula 2 is synthesized by a process comprising:

cross-coupling 2-halo-methoxy pyridine 4, wherein X is Cl or Br, with 3-halo-pyridin-4-amine 5 using a catalyst and a third base in a polar solvent, to produce bipyridylamine 6;

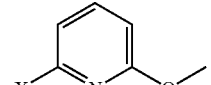

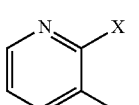

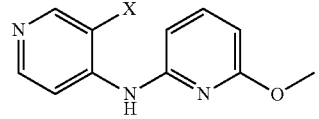

wherein the catalyst is
dichloro[9,9-dimethyl-4,5-bis(diphenylphosphino)xanthene]palladium(II),
the third base is cesium carbonate, and
the polar solvent is 1,4-dioxane;
cyclizing the compound of formula 6 to form 1,6-diazacarbazole 7;

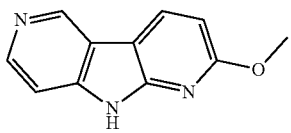

cleaving the methoxy group from the compound of formula 7 using strong acid to give an acid addition salt of a compound having formula 8;

and converting the compound of formula 8 into the compound of formula 2 wherein R is CF₃, with an activating agent in presence of a fourth base at a temperature between 0 and 50 C, wherein the activating agent is N,N-bis(trifluoromethyl-sulfonyl)aniline, and the fourth base is N,N-diisopropylethylamine.

12. The process of claim 11, wherein X is chloro.

13. The process of claim 1, wherein the polar solvent is a mixture of 1,4-dioxane and water.

14. The process of claim 7, wherein the organic or inorganic acid is acetic acid.

15. The process of claim 8, wherein the second base is triethylamine.

* * * * *